(12) United States Patent
DeGould

(10) Patent No.: US 7,758,526 B2
(45) Date of Patent: Jul. 20, 2010

(54) HAND AND DIGIT IMMOBILIZER FOR PULSE OXIMETER

(76) Inventor: Michael D. DeGould, 10927 Whispering Pines Way, Rockford, IL (US) 61114

(*) Notice: Subject to any disclaimer, the term of this patent is extended or adjusted under 35 U.S.C. 154(b) by 0 days.

(21) Appl. No.: 11/561,674

(22) Filed: Nov. 20, 2006

(65) Prior Publication Data

US 2008/0119700 A1 May 22, 2008

(51) Int. Cl.
*A61F 5/37* (2006.01)
*A41D 13/08* (2006.01)
*A41D 19/00* (2006.01)

(52) U.S. Cl. .......................... 602/21; 602/22; 128/878; 128/879; 128/880; 2/16; 2/159

(58) Field of Classification Search .................. 602/21, 602/22; 2/16, 21, 158, 159, 161.1, 163; 128/879, 128/880; 473/212, 213
See application file for complete search history.

(56) References Cited

U.S. PATENT DOCUMENTS

| | | | | |
|---|---|---|---|---|
| 2,314,545 | A * | 3/1943 | Lindfelt | 2/159 |
| 4,173,218 | A * | 11/1979 | Cronin | 602/21 |
| 4,510,939 | A | 4/1985 | Brenman et al. | |
| 4,706,658 | A * | 11/1987 | Cronin | 602/13 |
| 4,873,998 | A | 10/1989 | Joyner | |
| 4,982,744 | A * | 1/1991 | Stanec | 128/877 |
| 5,121,743 | A | 6/1992 | Bishop | |
| 5,140,998 | A | 8/1992 | Vickers | |
| 5,295,948 | A * | 3/1994 | Gray | 602/5 |
| 5,344,406 | A | 9/1994 | Spooner | |
| 5,560,375 | A | 10/1996 | Kabanek | |
| 5,776,059 | A | 7/1998 | Kaestle et al. | |
| 5,934,277 | A | 8/1999 | Mortz | |
| 6,010,473 | A | 1/2000 | Robinson | |
| 6,154,667 | A | 11/2000 | Miura et al. | |
| 6,199,211 | B1 * | 3/2001 | Franzolino | 2/161.6 |
| 6,224,548 | B1 | 5/2001 | Gopinathan | |
| 6,470,199 | B1 | 10/2002 | Kopotic et al. | |
| 6,482,168 | B1 | 11/2002 | Betcher | |
| 6,496,984 | B1 * | 12/2002 | Chow | 2/16 |
| 6,505,061 | B2 | 1/2003 | Larson | |
| 6,589,171 | B2 | 7/2003 | Keirsbilck | |
| 6,694,523 | B2 | 2/2004 | Hurst | |
| 6,808,502 | B2 * | 10/2004 | Nguyen | 602/21 |
| 2005/0101897 | A1 | 5/2005 | Froom | |
| 2005/0145255 | A1 | 7/2005 | Mengato | |

* cited by examiner

*Primary Examiner*—Patricia M Bianco
*Assistant Examiner*—Keri J Nicholson
(74) *Attorney, Agent, or Firm*—Quarles & Brady, LLP

(57) ABSTRACT

A hand and digit immobilizer prevents a patient from dislodging a pulse oximeter finger sensor by finger movement or fist clenching. In one form, the hand and digit immobilizer includes a glove body having a palm section and a back section defining a proximal opening for receiving a person's hand. The glove body has four finger base openings for receiving the fingers of the hand and has a thumb base opening for receiving the thumb. A finger covering section is connected to and extends away from each finger base opening. At least one finger covering section having a distal finger opening at its distal end. A rigid plate is secured to the palm section of the glove body and a palm side of each finger covering section such that clenching of the fingers is prevented thereby avoiding dislodging of a finger sensor from a fingertip.

23 Claims, 3 Drawing Sheets

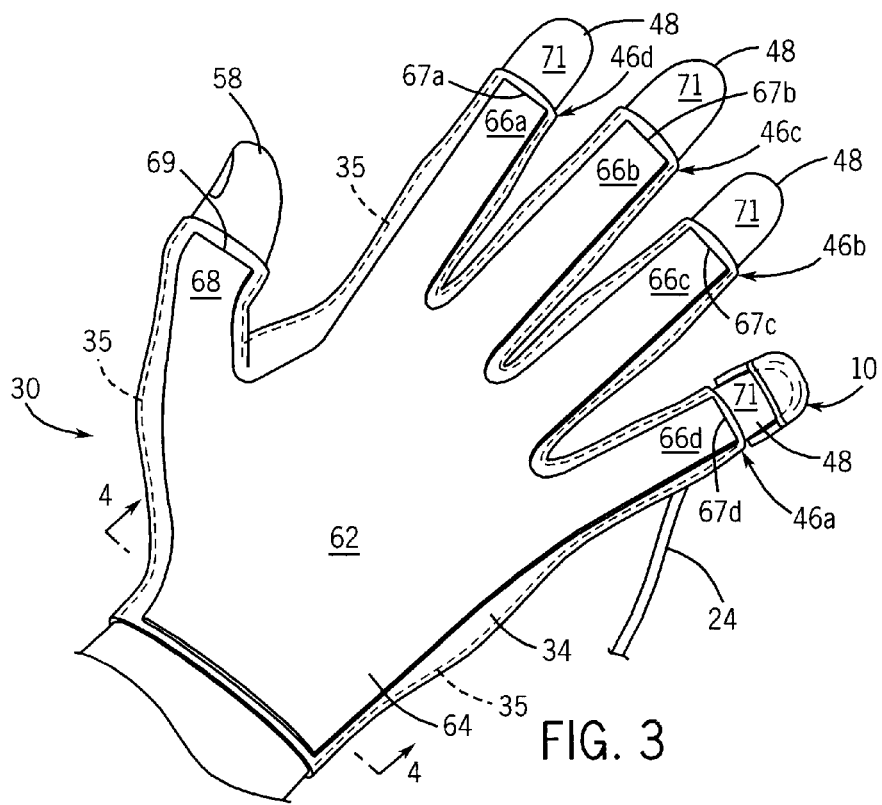
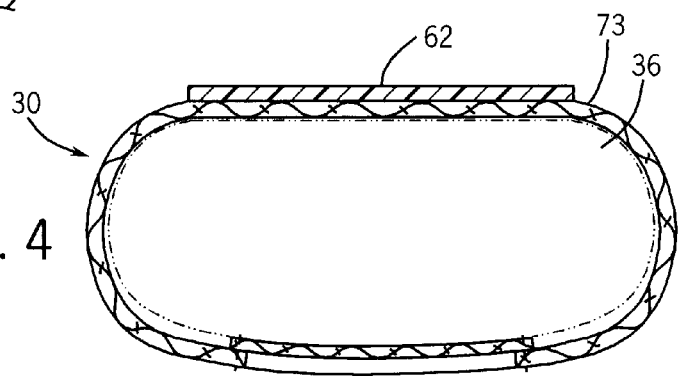
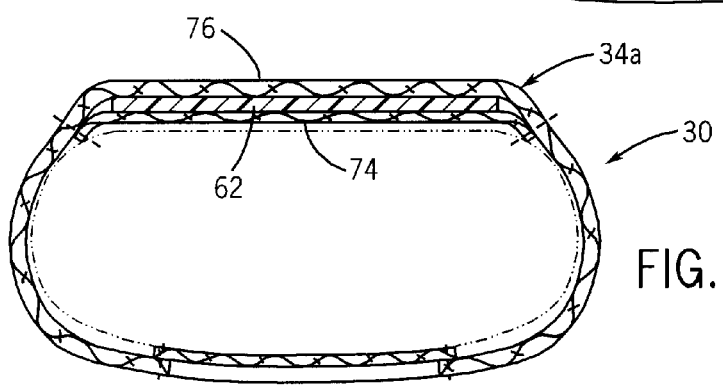

HAND AND DIGIT IMMOBILIZER FOR PULSE OXIMETER

CROSS-REFERENCES TO RELATED APPLICATIONS

Not Applicable.

STATEMENT REGARDING FEDERALLY SPONSORED RESEARCH

Not Applicable.

BACKGROUND OF THE INVENTION

1. Field of the Invention

This invention relates to a hand and digit immobilizer for preventing a patient from dislodging a pulse oximeter finger sensor by finger movement or fist clenching.

2. Description of the Related Art

Pulse oximetry is used in the medical profession for monitoring the oxygenation of patients during surgical procedures under general anesthesia, during outpatient and office based anesthetics, recovery room, emergency room, intensive care and ambulance environments. In typical pulse oximetry, use is made of a finger sensor into which is integrated at least one light source, such as a light emitting diode, on the emission side of the sensor and at least one photoreceiver which is located on the opposite reception side of the sensor. The light emitted by the light source is introduced into the tissue of the patient to be monitored and the photoreceiver measures the intensity of the light transmitted through the tissue. The intensity measured on the reception side can be used for calculating the oxygen saturation in the arterial blood of a patient.

FIG. 1 shows one example pulse oximetry sensor as described in U.S. Pat. No. 5,776,059. The sensor 10 has a first casing section 12 that houses the light source 14. During application, the sensor 10 is placed on a finger 16 of a patient and is fixed there with an adhesive. A second casing section 18 with elastic properties passes around the finger 16 and thus ensures mechanical fixing. The second casing section 18 includes the photoreceiver 22 which measures the intensity of the light radiated through the human finger tissue. The photoreceiver 22 is electrically connected to an electrical cable 24 that is connected to a processor and monitor where electrical signals are processed and measurements are displayed. An example processing circuit used in pulse oximetry is described in U.S. Pat. No. 5,934,277. It is noted that U.S. Pat. No. 5,776,059 shows one example finger sensor; however, finger sensors that use a clip type structure are also well known. See, for example, U.S. Pat. Nos. 6,505,061 and 6,154,667.

While existing pulse oximetry finger sensors are suitable for many applications, they do have drawbacks. Namely, involuntary patient movement can dislodge finger sensors. For example, fist clenching, finger movement, and fidgeting with the finger sensor will often dislodge or even break pulse oximetry finger sensors. This results in false readings, motion artifact, and wasted time during surgery or the particular monitoring event by the necessity of constant replication or adjustment of the finger sensor. Additionally, broken finger sensors can be costly to replace.

Accordingly, there is a need for a means for preventing a patient from dislodging a finger sensor by finger movement or fist clenching. Such a device should be safe, easy to apply and remove, be disposable depending on environment, while holding the hand and fingers safely in a neutral position without compression of the skin or underlying nervous or vascular structures.

SUMMARY OF THE INVENTION

The foregoing needs are met by the present invention which provides a hand and digit immobilizer for preventing a patient from dislodging a finger sensor by finger movement or fist clenching.

In one aspect of the invention, the hand and digit immobilizer includes a glove body having a palm section and a back section defining a proximal opening for receiving a person's hand at a proximal end of the glove body. The glove body has at least one finger base opening for receiving a finger of the hand. At least one finger covering section is connected to and extends away from a finger base opening for receiving a finger. At least one finger covering section has a distal finger opening at its distal end that allows the fingertip to be exposed when the hand and digit immobilizer is placed on a person's hand. The exposed fingertip provides a site for application of a finger sensor such as the example sensors mentioned above. A rigid plate is secured to the palm section of the glove body and a palm side of a finger covering section having the distal finger opening such that clenching of the finger covered by the finger covering section having the distal finger opening is prevented thereby avoiding dislodgement of a finger sensor from the fingertip. Preferably, the rigid plate is dimensioned such that the rigid plate extends distally beyond a distal knuckle of a finger within the finger covering section having the distal finger opening.

The glove body may also have a thumb base opening for receiving the thumb of the hand, and a thumb covering section may be connected to and extend away from the thumb base opening. The rigid plate may be secured to a palm side of the thumb covering section such that clenching of the thumb is prevented. The thumb covering section may have a distal thumb opening at its distal end that allows the tip of the thumb to be exposed when the hand and digit immobilizer is placed on a person's hand. The exposed tip of the thumb provides another site for application of a finger sensor.

Additionally, sections of the rigid plate secured to the palm side of the finger covering sections and thumb section may be adjustable to accommodate fingers and thumbs of different lengths.

In one form, the glove body has four finger base openings for receiving the fingers of the hand, and four finger covering sections are connected to and extend away from the finger base openings for receiving four fingers. The rigid plate may be secured to a palm side of the four finger covering sections such that clenching of the four fingers is prevented. Optionally, each of the four finger covering sections includes a distal finger opening at its distal end such that each fingertip is exposed when the hand and digit immobilizer is placed on a person's hand. The exposed fingertips provide four sites for application of a finger sensor.

The palm section and the back section of the glove body may comprise a fabric such that the hand and fingers are held safely in a neutral position without compression of the skin or underlying nervous or vascular structures. The back section of the glove body may include an elastic material allowing for variations in hand size. The elastic material may comprise part or all of the back section. The rigid plate may be secured within layers of the glove body fabric, or the rigid plate may be secured to an outside or inside surface of the glove body.

In another form, the back section of the glove body has a cutaway section defining spaced apart inner edges, and an elastic material is connected to the spaced apart inner edges such that the glove body can expand to fit hands of different sizes. The elastic material may be an elastic mesh, or the elastic material may be one or more elastic bands.

In another aspect of the invention, the hand and digit immobilizer includes a glove body having a palm section and a back section defining a proximal opening for receiving a person's hand at a proximal end of the glove body. The glove body has four finger base openings for receiving the fingers of the hand and also has a thumb base opening for receiving the thumb of the hand. A finger covering section is connected to and extends away from each finger base opening. At least one finger covering section has a distal finger opening at its distal end that allows the fingertip to be exposed when the hand and digit immobilizer is placed on a person's hand. A rigid plate is secured to the palm section of the glove body and a palm side of each finger covering section such that clenching of the fingers is prevented thereby avoiding dislodgement of a finger sensor from the fingertip. Optionally, each finger covering section may have a distal finger opening at its distal end. Preferably, the rigid plate is dimensioned such that the rigid plate extends distally beyond a distal knuckle of a finger within each finger covering section.

In yet another aspect of the invention, the hand and digit immobilizer includes a glove body having a palm section and a back section comprising an elastic material. The palm section and the back section define a proximal opening for receiving a person's hand at a proximal end of the glove body. The glove body has at least one finger base opening for receiving a finger of the hand. At least one finger covering section is connected to and extends away from a finger base opening. At least one finger covering section has a distal finger opening at its distal end. The palm section of the glove body is rigid and a palm side of a finger covering section having the distal finger opening is rigid such that clenching of the finger covered by the finger covering section having the distal finger opening is prevented thereby avoiding dislodgement of a finger sensor from the finger tip. Preferably, the finger covering section having the distal finger opening is dimensioned such that the finger covering section having the distal finger opening extends distally beyond a distal knuckle of a finger within the finger covering section having the distal finger opening.

In still another aspect of the invention, a method is provided for performing a medical measurement on a finger of a patient. In the method, a hand and digit immobilizer according to the invention is placed on the patient's hand, and a medical measurement sensor is applied to the tip of the finger. The method prevents a patient from dislodging the sensor by finger movement or fist clenching.

In one example form, the invention provides a canvas glove without fingertips allowing the exposure of the fingernail bed and finger tip pads for application of a pulse oximeter finger tip sensor. The dorsum of the glove has a band of elastic mesh allowing for variations in adult hand size, and the palmar surface of the palm and fingers is impregnated with rigid, non-bendable, fiberglass cast resin used in orthopedics, or dental methylmethacrylate resin.

Thus, it is an advantage of the present invention to provide a glove that prevents independent finger and thumb movement and fist clenching, allowing a pulse oximeter finger sensor to remain in place on the thumb or finger tip undisturbed by patient motion.

These and other features, aspects, and advantages of the present invention will become better understood upon consideration of the following detailed description, drawings, and appended claims.

BRIEF DESCRIPTION OF THE DRAWINGS

FIG. 3 is a palm view of hand and digit immobilizer of FIG. 2.

FIG. 4 is a cross-sectional view taken along line 4-4 of FIG. 3.

FIG. 5 is a cross-sectional view similar to FIG. 4 of another embodiment of the hand and digit immobilizer.

Like reference numerals will be used to refer to like parts from Figure to Figure in the following description of the drawings.

DETAILED DESCRIPTION

Figure 1:
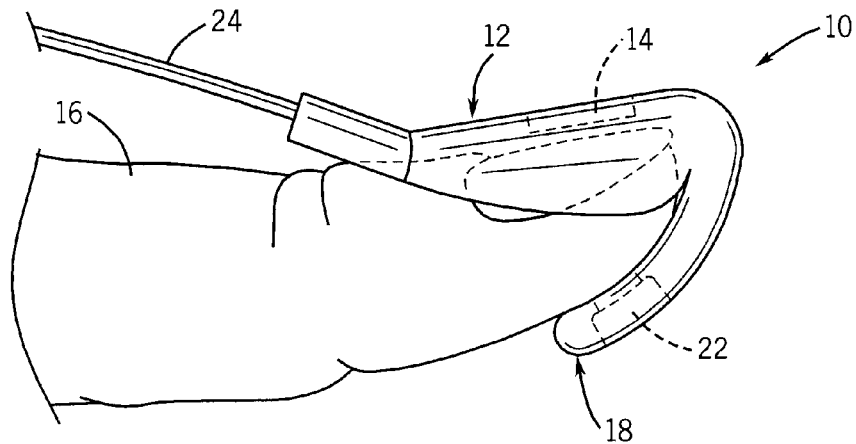
FIG. 1 is a side view of an example prior art pulse oximetry sensor applied to a human finger.
Figure 2:
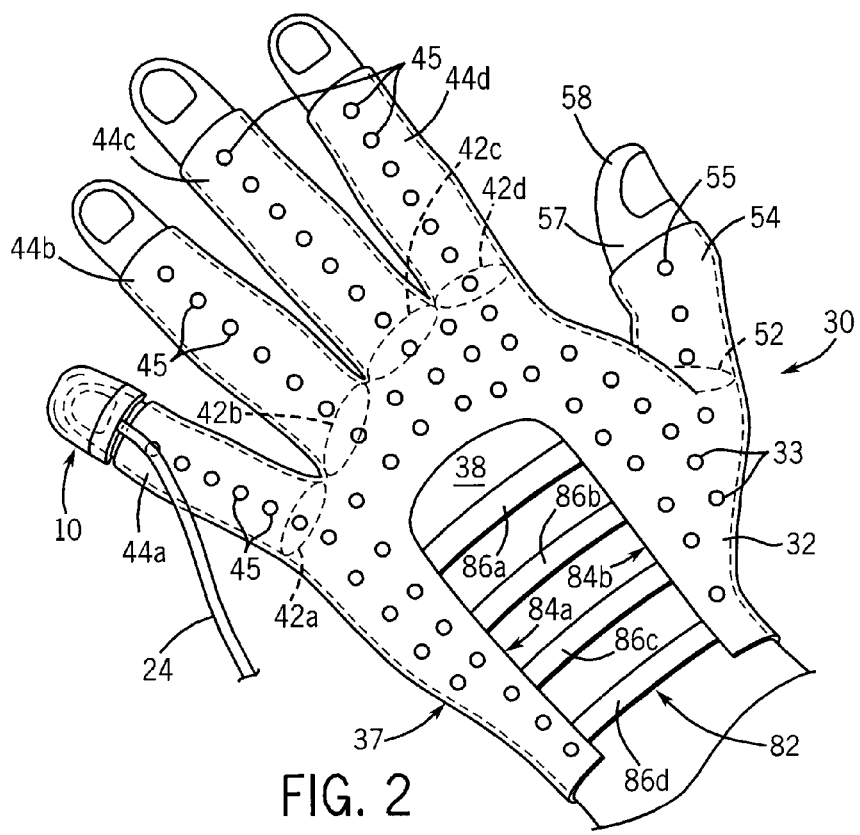
FIG. 2 is a back view of a hand and digit immobilizer according to the invention.

Turning to FIGS. 2 to 4, there is shown a hand and digit immobilizer 30 according to the invention. The hand and digit immobilizer 30 includes a back section 32 having optional ventilation holes 33 and includes a palm section 34. The back section 32 and the palm section 34 may be secured together by suitable means such as stitching 35. Together, the back section 32 and the palm section 34 provide a glove body 37 that defines a proximal opening 36 for receiving a person's hand 38. The glove body 37 includes finger base openings 42a, 42b, 42c, 42d for receiving the fingers 16 of the hand 38. The fingers 16 are inserted through the finger base openings 42a, 42b, 42c, 42d of the glove body 37 when placing the hand and digit immobilizer 30 on the person's hand 38.

The hand and digit immobilizer 30 also includes finger covering sections 44a, 44b, 44c, 44d that are connected to and extend away from the finger base openings 42a, 42b, 42c, 42d, respectively. The fingers 16 are inserted into the finger covering sections 44a, 44b, 44c, 44d when placing the hand and digit immobilizer 30 on the person's hand 38. The back side of each finger covering section 44a, 44b, 44c, 44d optionally includes ventilation holes 45. Each finger covering section 44a, 44b, 44c, 44d has a distal finger opening 46a, 46b, 46c, 46d respectively at its distal end. The distal finger openings 46a, 46b, 46c, 46d provide a means for exposing fingertips 48a, 48b, 48c, 48d and thereby provide a site for application of a finger sensor such as the example sensors mentioned above. In FIGS. 2 and 3, the sensor 10 is shown applied to one finger. However, any number of sensors may be applied to any of the fingers and/or thumb. Also, while four distal finger openings are shown, one or more may be suitable for use in the hand and digit immobilizer 30. In other words, some finger covering sections may not have a distal finger opening.

The hand and digit immobilizer 30 also includes a thumb covering section 54 that is connected to and extends away from a thumb base opening 52 of the glove body 37. The thumb 57 is inserted into the thumb covering section 54 when placing the hand and digit immobilizer 30 on the person's hand 38. The back side of the thumb covering section 54 optionally includes ventilation holes 55. The thumb covering section 54 has a distal thumb opening 56 at its distal end. The distal thumb opening 56 provides a means for exposing the thumb tip 58 and thereby provides a site for application of a finger sensor such as the example sensors mentioned above to the tip of the thumb. Optionally, the thumb covering section 54 may not have a distal opening.

The hand and digit immobilizer 30 also includes a rigid plate 62 that is secured to the palm section 34 of the hand and digit immobilizer 30. The rigid plate 62 includes a palm section 64, finger sections 66a, 66b, 66c, 66d and a thumb section 68. When the hand and digit immobilizer 30 is placed on a person's hand 38, the rigid plate 62 is located near the palm of the person's hand and the palm side 71 of the fingers 16. The compressive forces of the back section 32 and the palm section 34 of the glove body 37 serve to keep the person's thumb 57 and fingers 16 near the rigid plate 62 during a medical procedure. Preferably, the finger sections 66a, 66b, 66c, 66d of the rigid plate 62 are dimensioned such that the ends 67a, 67b, 67c and 67d of the finger sections 66a, 66b, 66c, 66d extend beyond a distal knuckle of each finger to best prevent finger clenching. Likewise, the thumb section 68 of the rigid plate 62 is dimensioned such that the end 69 of the thumb section 68 extends beyond a distal knuckle of the thumb 57 to best prevent thumb clenching.

The rigid plate 62 may be secured to the glove body 37 in a number of manners. FIGS. 4 and 5 show two examples. In FIG. 4, the rigid plate 62 is secured to an outside surface 73 of the palm section 34 and palm side of each finger covering section 44a, 44b, 44c, 44d. In FIG. 5, the rigid plate 62 is secured within an inner layer 74 and an outer layer 76 of an alternative palm section 34a. The rigid plate 62 may also be secured to an inner surface of the palm section 34 and the inner surface of each finger covering section 44a, 44b, 44c, 44d. Regardless of the positioning of the rigid plate 62 in or on the palmar regions of the hand and digit immobilizer 30, the glove body 37, the finger covering sections 44a, 44b, 44c, 44d, and the rigid plate 62 serve to prevent finger and thumb clenching.

As an alternative to the use of a rigid plate, the palm section 34 of the glove body 37 and the palm side of each finger covering section 44a, 44b, 44c, 44d may be formed with a rigid material such that the palm section 34 of the glove body 37 is rigid and the palm side of each finger covering section 44a, 44b, 44c and 44d is rigid such that clenching of the finger covered by the finger covering section having the distal finger opening is prevented. One method for forming this version of the hand and digit immobilizer 30 involves forming the palm section 34 of the glove body 37 and the palm side of each finger covering section 44a, 44b, 44c, 44d from a porous material and impregnating the porous material with a curable material that thereafter hardens to form the rigid palm section 34 of the glove body 37 and the rigid palm side of each finger covering section 44a, 44b, 44c and 44d. Curable resins such as the fiberglass cast resin used in orthopedics or dental methylmethacrylate resin are non-limiting examples.

Figure 6:
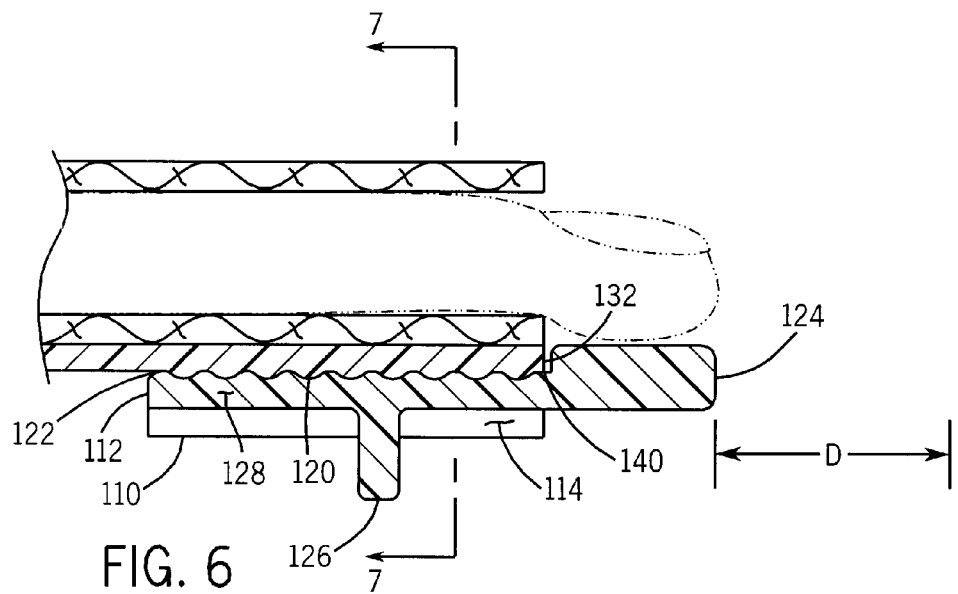
FIG. 6 is a cross-sectional view of another embodiment of the hand and digit immobilizer.
Figure 7:
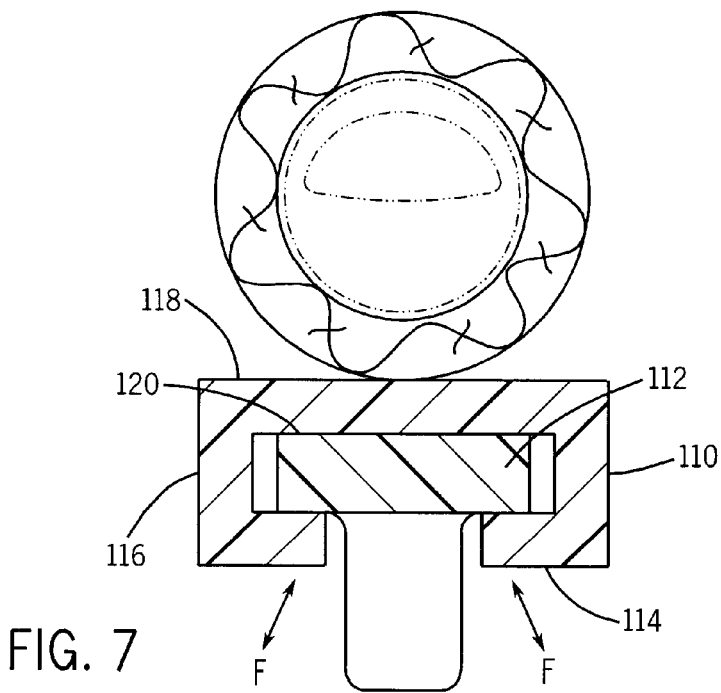
FIG. 7 is a cross-sectional view along line 7-7 of FIG. 6.

Turning to FIGS. 6 and 7, as an alternative to using a single rigid plate 62, one or more of the finger sections 66a, 66b, 66c, 66d, and thumb section 68 may be constructed of a channel section 110 and an adjustable section 112. This embodiment allows for the length of the finger sections 66a, 66b, 66c, 66d, and the thumb section 68 to be easily adjusted, (i.e., extended and retracted in the D directions (as shown in FIG. 6)), to accommodate differing finger 16 and thumb 57 lengths.

In the present embodiment, the channel section 110 has a cross-section including L-shaped tabs 114, 116 extending downwardly from a horizontal upper shoulder 118. The lower face 120 of the horizontal upper shoulder 118 and the L-shaped tabs 114, 116 are configured to engage the adjustable section 112. The contours 122 of the lower face 120 may have a wave-like structure (as shown in FIG. 6), a saw-tooth configuration, a ratchet configuration, or any suitable contour providing resistance against undesired movement of the adjustable section 112 in the D directions.

The adjustable section 112 has a head section 124, a finger tab 126, and a contoured section 128. The head section 124 is located at the distal end of the adjustable section 112 and is sized to support the distal end of a finger 16 or thumb 57. The finger tab 126 extends downwardly from the adjustable section 124 and allows force to be applied to the adjustable section 112 in the D directions to facilitate movement of the adjustable section 112 relative to the channel section 110. The upper face 140 of the contoured section 128 is configured to engage the contours 122 present in the lower face 120 of the horizontal upper portion 118 of the channel section 110. Alternatively, the lower face 120 and the upper face 140 may be substantially flat and rely upon a limited interference fit to provide the requisite resistance in the D directions.

The adjustable section 112 is slidably engaged within the channel section 110 in the D directions (as shown on FIG. 6). To extend the adjustable section 112, force is applied to the finger tab 126 to move the adjustable section 112 towards the distal end of a finger 16 or thumb 57. The contoured section 128 of the adjustable section 112 rides along the contours 122 of the channel section 110. The L-shaped tabs 114, 116 of the channel section 110 deflect slightly in the F direction (as show in FIG. 7) and allow the adjustable section 112 to move relative to the channel section 110 in the D directions. Retraction of the adjustable section 112 operates in the same manner when force is applied to move the adjustable section 112 away from the distal end of a finger 16 or thumb 57. Retraction is restrained when the head section 124 contacts the end face 132 of the channel section 110.

The channel section 110, adjustable section 112, and rigid plate 62 may be constructed from various materials, including but not limited to, plastics, metals, composites, and the like, and may be provided in sizes suitable for adult hands and child hands.

The hand and digit immobilizer 30 serves to hold the hand and fingers and thumb safely in a neutral position without compression of the skin or underlying nervous or vascular structures. In this regard, various materials and constructions are suitable for the glove body 37, finger covering sections 44a, 44b, 44c, 44d, and thumb covering section 54. In one example construction, the glove body 37, finger covering sections 44a, 44b, 44c, 44d, and thumb covering section 54 are formed from an elastomeric material. Example elastomeric materials include latex rubber. In another example construction, the glove body 37, finger covering sections 44a, 44b, 44c, 44d, and thumb covering section 54 are formed from an elasticized material such as a non-woven or woven material incorporating elastic materials. The glove body 37, finger covering sections 44a, 44b, 44c, 44d, and thumb covering section 54 may also be formed from stretchable, resilient looped yarn filaments. The glove body 37, finger covering sections 44a, 44b, 44c, 44d, and thumb covering section 54 may also be formed from elastomeric materials such as stretch nylon and elastomeric polyurethane materials (e.g., spandex). Other equivalent cloth materials (e.g., canvas) are also suitable.

The hand and digit immobilizer 30 may be provided in various sizes for fitting adult hands and child hands. The use of elastic materials described above may also provide for universal sizing for different hand sizes. Various constructions of the glove body 37 may also provide for universal sizing. For example, FIG. 2 shows one example construction for accommodating hands of various sizes. The back section 32 has a cutaway section 82 that defines opposed inner edges 84a, 84b for the back section 32. Elastic bands 86a, 86b, 86c, 86d connect the opposed inner edges 84a, 84b such that the distance between the opposed inner edges 84a, 84b can vary depending on the size of the hand 38. This provides for a custom fit for the hand and digit immobilizer 30. Alternatively, the back section may not have the cutaway section 82 but may comprise an elastic material (such as spandex) to provide a custom fit for the hand and digit immobilizer 30. In another version of the hand and digit immobilizer 30, the entire space created by the cutaway section 82 may comprise an elastic material (such as spandex).

Therefore, the hand and digit immobilizer 30 may be used in a method for performing a medical measurement on a finger of a patient. In the method, a hand and digit immobilizer 30 according to the invention is placed on the patient's hand, and a medical measurement sensor is applied to the tip of the finger. The method prevents a patient from dislodging the sensor by finger movement or fist clenching. The hand and digit immobilizer is safe, easy to apply and remove, may be disposable, and holds the hand and fingers safely in a neutral position without compression of the skin or underlying nervous or vascular structures.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A hand and digit immobilizer comprising:
    a glove body having a palm section and a back section defining a proximal opening for receiving a person's hand at a proximal end of the glove body, the glove body having at least one finger base opening for receiving a finger of the hand;
    at least one finger covering section connected to and extending away from a finger base opening, the at least one finger covering section having a distal finger opening at its distal end; and
    a single rigid plate secured to the palm section of the glove body and a palm side of a finger covering section having the distal finger opening such that clenching of the finger covered by the finger covering section having the distal finger opening is prevented,
    wherein the glove body is dimensioned such that the proximal end of the glove body terminates at the wrist, and
    wherein the rigid plate is dimensioned such that the rigid plate extends distally beyond a distal knuckle of a finger within the finger covering section having the distal finger opening, and
    wherein the rigid plate is dimensioned such that a proximal end of the rigid plate terminates at the wrist.

2. The hand and digit immobilizer of claim 1 wherein:
    a section of the rigid plate secured to the palm side of the at least one finger covering section is adjustable to accommodate fingers of different lengths.

3. The hand and digit immobilizer of claim 2 wherein:
    the section of the rigid plate includes a channel configured to engage an adjustable section such that the adjustable section can extend and retract.

4. The hand and digit immobilizer of claim 1 wherein:
    the glove body has a thumb base opening for receiving the thumb of the hand,
    the hand and digit immobilizer includes a thumb covering section connected to and extending away from the thumb base opening, and
    the rigid plate is secured to a palm side of the thumb covering section such that clenching of the thumb is prevented.

5. The hand and digit immobilizer of claim 4 wherein:
    a section of the rigid plate secured to a palm side of the thumb covering section is adjustable to accommodate thumbs of different lengths.

6. The hand and digit immobilizer of claim 4 wherein:
    the glove body has four finger base openings for receiving the fingers of the hand, and
    the hand and digit immobilizer has four finger covering sections connected to and extending away from the finger base openings.

7. The hand and digit immobilizer of claim 6 wherein:
    the rigid plate is secured to a palm side of the four finger covering sections such that clenching of the four fingers is prevented.

8. The hand and digit immobilizer of claim 6 wherein:
    each of the four finger covering sections includes a distal finger opening at its distal end.

9. The hand and digit immobilizer of claim 1 wherein:
    the palm section and the back section of the glove body comprise a fabric.

10. The hand and digit immobilizer of claim 1 wherein:
    the back section of the glove body includes an elastic material.

11. The hand and digit immobilizer of claim 1 wherein:
    the rigid plate is secured within layers of the glove body.

12. The hand and digit immobilizer of claim 1 wherein:
    the rigid plate is secured to an outside surface of the glove body.

13. The hand and digit immobilizer of claim 1 wherein:
    the back section of the glove body has a cutaway section defining spaced apart inner edges, and
    an elastic material is connected to the spaced apart inner edges such that the glove body can expand to fit hands of different sizes.

14. The hand and digit immobilizer of claim 13 wherein:
    the elastic material is an elastic mesh.

15. The hand and digit immobilizer of claim 13 wherein:
    the elastic material comprises at least one elastic band.

16. The hand and digit immobilizer of claim 1 wherein:
    the rigid plate includes spaced apart finger sections.

17. A method for performing a medical measurement on a finger of a patient, the method comprising:
    placing the hand and digit immobilizer according to claim 1 on the patient's hand; and
    applying a medical measurement sensor to the tip of the finger.

18. A hand and digit immobilizer comprising:
    a glove body having a palm section and a back section defining a proximal opening for receiving a person's hand at a proximal end of the glove body, the glove body having four finger base openings for receiving the fingers of the hand and having a thumb base opening for receiving the thumb of the hand;
    a finger covering section connected to and extending away from each finger base opening, at least one finger covering section having a distal finger opening at its distal end; and
    a single rigid plate secured to the palm section of the glove body and a palm side of each finger covering section such that clenching of the fingers is prevented,
    wherein the glove body is dimensioned such that the proximal end of the glove body terminates at the wrist, and wherein the rigid plate is dimensioned such that the rigid plate extends distally beyond a distal knuckle of a finger within each finger covering section, and wherein the rigid plate is dimensioned such that a proximal end of the rigid plate terminates at the wrist.

19. The hand and digit immobilizer of claim 18 wherein:
a section of the rigid plate secured to the palm side of at least one finger covering section includes at least one adjustable section to accommodate fingers of different lengths.

20. The hand and digit immobilizer of claim 19 wherein:
the section of the rigid plate includes a channel configured to engage an adjustable section such that the adjustable section can extend and retract.

21. The hand and digit immobilizer of claim 18 wherein:
each finger covering section has a distal finger opening at its distal end.

22. The hand and digit immobilizer of claim 18 wherein:
the rigid plate includes spaced apart finger sections.

23. A method for performing a medical measurement on a finger of a patient, the method comprising:
placing the hand and digit immobilizer according to claim 18 on the patient's hand; and
applying a medical measurement sensor to the tip of the finger.

* * * * *